US008431140B2

(12) United States Patent
Lindahl et al.

(10) Patent No.: US 8,431,140 B2
(45) Date of Patent: Apr. 30, 2013

(54) TOPICAL COMPOSITIONS

(75) Inventors: Ake Lindahl, Malmo (SE); Birgitta Svensson, Malmo (SE); Anna Holmberg, Lund (SE); Johan Engblom, Lund (SE)

(73) Assignees: Dr. Reddy's Laboratories, Inc., Bridgewater, NJ (US); Dr. Reddy's Laboratories, Ltd., Hyderabad (IN)

( * ) Notice: Subject to any disclaimer, the term of this patent is extended or adjusted under 35 U.S.C. 154(b) by 584 days.

(21) Appl. No.: 12/304,420

(22) PCT Filed: Jun. 14, 2007

(86) PCT No.: PCT/US2007/071212
§ 371 (c)(1),
(2), (4) Date: Dec. 11, 2008

(87) PCT Pub. No.: WO2007/147052
PCT Pub. Date: Dec. 21, 2007

(65) Prior Publication Data
US 2009/0247529 A1 Oct. 1, 2009

Related U.S. Application Data

(60) Provisional application No. 60/813,372, filed on Jun. 14, 2006, provisional application No. 60/820,542, filed on Jul. 27, 2006, provisional application No. 60/820,546, filed on Jul. 27, 2006.

(51) Int. Cl.
*A61K 8/02* (2006.01)
*A61K 31/135* (2006.01)

(52) U.S. Cl.
USPC .......................................... 424/401; 514/655

(58) Field of Classification Search .................. None
See application file for complete search history.

(56) References Cited

U.S. PATENT DOCUMENTS

| 4,767,751 A | 8/1988 | Davis |
| 4,940,701 A | 7/1990 | Davis |
| 6,083,518 A | 7/2000 | Lindahl |
| 6,537,576 B1 | 3/2003 | Lindahl et al. |
| 2005/0036953 A1 | 2/2005 | Arkin et al. |
| 2005/0042268 A1 | 2/2005 | Aschkenasy et al. |
| 2005/0181999 A1* | 8/2005 | Ferrandis et al. ............... 514/28 |
| 2005/0196418 A1* | 9/2005 | Yu et al. ........................ 424/401 |

FOREIGN PATENT DOCUMENTS

| WO | 97/10812 A2 | 3/1997 |
| WO | 99/58109 A1 | 11/1999 |
| WO | 00/24966 A1 | 5/2000 |
| WO | 02/070455 A1 | 9/2002 |
| WO | 2005/016329 A1 | 2/2005 |

OTHER PUBLICATIONS

W. L. Chiou and S. Riegelmann, Journal of Pharmaceutical Science, vol. 60, No. 9, pp. 1281-1302, 1971.
Coldman, et al., Journal of Pharmaceutical Science, vol. 58, No. 9, pp. 1098-1102, 1969.
J. M. Wood, "Osmosensing by Bacteria: Signals and Membrane-Based Sensors", Microbiology Molecular Biology Review, vol. 63, No. 1, pp. 230-262, Mar. 1999.

* cited by examiner

*Primary Examiner* — Shengjun Wang
*Assistant Examiner* — Svetlana M Ivanova
(74) *Attorney, Agent, or Firm* — Edward D. Pergament; Milagros A. Cepeda; Pergament Gilman & Cepeda LLP

(57) ABSTRACT

Single phase pharmaceutical compositions for topical application, in addition to kits and methods of use and administration are provided. The compositions comprise a biologically active agent; a delivery vehicle comprising at least a non-polymeric crystallization inhibitor and a film-former; and a volatile solvent; wherein the biologically active agent is present in the composition in a subsaturated state, the biologically active agent is present in the delivery vehicle in a supersaturated state, and the crystallization inhibitor is capable of delaying crystallization of the biologically active agent in the delivery vehicle. Biologically active agents include terbinafine and acyclovir. Treatments for onychomycosis and Varicella zoster infection, HSV-I infection or HSV-2 infection are provided.

42 Claims, No Drawings

TOPICAL COMPOSITIONS

CROSS-REFERENCE TO RELATED APPLICATIONS

This application claims the benefit of priority from provisional U.S. Application Nos. 60/813,372, filed Jun. 14, 2006, 60/820,542, filed Jul. 27, 2006, and 60/820,546, filed Jul. 27, 2006, the disclosures of which are hereby incorporated by reference in their entireties.

TECHNICAL FIELD

The present invention relates to single phase topical compositions containing a biologically active agent in a delivery vehicle having a volatile component. The biologically active agent is to be released from the composition upon application thereof.

BACKGROUND

Topical delivery of a pharmaceutical agent depends on the ability of the agent to be released from its formulation and subsequently permeate a barrier, such as skin, nails, and/or hooves, to get to an area in need of such treatment. Non-invasive methods that require minimal management by a patient are preferred.

Certain methods, such as iontophoresis, rely on creating an electrical potential gradient over the barrier to enhance permeation of the pharmaceutical agent. These methods are primarily directed to drugs having a net charge.

For most drugs, including those that are uncharged or zwitterionic, methods that focus on a chemical potential of a drug in a carrier are useful. The flux of a drug into the body can be enhanced by increasing the chemical potential of the drug in its carrier. This is normally performed by chemical optimization of the drug composition by adjusting the degree of saturation of the drug in the carrier. Advantages to this approach are that the properties of the barrier itself are comparatively less affected and the lag time of initiation for the pharmacological effect is reduced. Two aspects to this approach include: i) creation of an initial high chemical potential of the drug in the composition, and ii) maintenance of a high chemical potential of the drug in the vicinity of the barrier after the application of the composition. It is usually desirable to prepare pharmaceutical compositions which are saturated with respect to the drug. During application, another aspect of the composition is that the solubility and diffusion properties of the drug in the used vehicle must preclude depletion of the drug in the vicinity of the barrier. Examples of compositions used for this purpose are microemulsions and emulsions.

Another approach towards keeping the composition saturated is the use of an excess amount of drug (non-solubilised) in the carrier, whereby the drug is subsequently dissolved as it replaces the drug which has penetrated through the barrier.

Yet another approach is the use of a supersaturated composition of the drug. Here, the driving force of the drug to penetrate the barrier is higher than in the saturated composition, since the drug in a supersaturated composition has higher chemical potential in comparison with the corresponding saturated composition. For example, such compositions have been prepared according to the following means or principles: i) dissolving the drug at temperatures and/or pressures at which the solubility of the drug is higher as compared to those temperatures and/or pressures that are relevant for medication (W. L. Chou and S. Riegelmann, J. Pharm. Sci., Vol. 60, No. 9, pp. 1281-1302, 1971; WO 97/10812), ii) mixing a saturated drug solution with a non-solvent therefor, thereby performing a merely physical operation, in situ or prior to application, with or without the presence of an anti-nucleating agent (U.S. Pat. No. 4,940,701, U.S. Pat. No. 4,767,751), iii) solvent evaporation to the surrounding air (Coldman et al., J. Pharm. Sci., 58, No. 9 (1969), pp. 1098-1102), iv) solvent penetration into the human body, v) water uptake into the composition from the human body, or vi) pH-changes in the composition caused by H+ uptake from the human body.

U.S. Pat. No. 6,083,518 discloses a biologically active composition comprising a solution of an active agent dissolved in a glass-forming carrier, which carrier comprises a glass-forming substance containing a plasticizer.

U.S. Pat. No. 6,537,576 relates to a novel biologically active composition which comprises a biologically active agent to be released therefrom, said biologically active agent being dissolved and/or dispersed in a supersaturated state within a carrier, which carrier comprises a liquid and/or solid non-crystalline ester and/or polyester matrix, and where the precipitation of said biologically active agent is substantially, or completely, inhibited therein.

From cosmetic perspective the amount of formulation (e.g., ointment, cream, gel, lotion, stick etc.) that may be applied on a body surface is limited to the range of about 1-10 $mg/cm^2$, thus producing a thin film with a surface to volume ratio favoring evaporation of volatile parts. The formulation therefore inevitably undergoes rapid changes in composition. The limited amount of formulation that may be applied further emphasizes drug accessibility as an important factor for penetration.

Certain drug carriers are prone to phase separation based on the content of solvents and polymers in the carriers. It is desirable to have topical compositions of a single phase to ensure uniform application and efficient use of the active drug.

There is an ongoing need to provide stable topical compositions that permit increased bioavailability of pharmaceutical agents to areas in need.

SUMMARY

Topical compositions containing a biologically active agent, a delivery vehicle, and a volatile solvent, in addition to kits and methods of use, manufacturing, and treatment are provided. In one aspect of the present invention, provided is a single phase pharmaceutical composition for topical application comprising: a biologically active agent; a delivery vehicle comprising a non-polymeric crystallization inhibitor that is capable of delaying crystallization of the biologically active agent in the delivery vehicle and a film-former; and a volatile solvent; wherein the biologically active agent is present in the composition in a subsaturated state, and wherein the biologically active agent is in a supersaturated state in the delivery vehicle, upon evaporation of the volatile solvent. In one or more embodiments, the composition further comprises a plasticizer.

The term "composition" means the product in its entirety, and the composition is packaged as desired into a tube or the like. By reference to "delivery vehicle," it is meant the portion of the composition carrying the biologically active agent that is intended not to evaporate and that stays on the area of treatment after the volatile component evaporates. The term "volatile solvent" means the portion of the composition that evaporates after application of the composition. That is, "volatile solvent" refers to one or more solvents including a co-solvent, if used, that leave a carrier, such as the delivery vehicle, within less than 24 hours at a specified chosen temperature, typically at room temperature of approximately 23° C., so that the presence of the solvent in the composition is fleeting. Moreover, the "volatile solvent" is capable of dissolving the biologically active agent.

In one embodiment, the volatile solvent has a vapor pressure at 20° C. of 0.5 kPa or greater; in a detailed embodiment, the vapor pressure is 2 kPa or greater; in a more detailed embodiment, the vapor pressure is 5 kPa or greater.

Generally, the compositions are prepared such that in the composition as a whole, the biologically active agent is in a subsaturated state. That is, the entire amount of biologically active agent present is dissolved in the composition. When the volatile component(s) evaporate, the agent is then present in the delivery vehicle in a supersaturated state.

By reference to "a non-polymeric crystallization inhibitor" it is meant to include compounds that are considered antinucleating agents, that is, agents that delay or prevent precipitation of a compound such as the biologically active agent. A crystallization inhibitor is, for example, an agent that can prevent crystallization of an active compound for extended periods of time, for example, 2, 4, 8, 12, or even 24 hours or more when the active compound is being supersaturated due to evaporation of a solvent.

In one or more embodiments, the volatile solvent comprises acetic acid, acetone, 1-butanol, 2-butanol, butyl acetate, tert-butylmethyl ether, ethanol, ethyl acetate, ethyl ether, ethyl formate, formic acid, heptane, isobutyl acetate, isopropyl acetate, methyl acetate, methylethyl ketone, methylisobutyl ketone, 2-methyl-1-propanol, pentane, 1-propanol, 2-propanol, propylacetate, water, n-butyl ether, isopropanol, or combinations thereof.

In one embodiment, the non-polymeric crystallization inhibitor comprises a hydroxycarboxylic acid. In a detailed embodiment, the hydroxycarboxylic acid comprises citric acid, lactic acid, malic acid, or combinations thereof.

In one or more embodiments, the non-polymeric crystallization inhibitor renders the composition stable for at least approximately 24 hours after administration. According to an embodiment of the invention, a composition can be considered stable if there is an absence of crystallization of the biologically active agent in the delivery vehicle for up to approximately 2 (or in other embodiments 4, 8, 12, or even 24) hours after administration of the composition. In one or more embodiments, a composition can also be considered stable if flux of the active ingredient after application remains above an acceptable rate over the shelf-life of the composition. The acceptable rate is specific to the active ingredient of interest and would be understood by one skilled in the art. In an embodiment, the composition remains stable in a suitable storage container for a period of 3 (or in other embodiments 6, 9, 12, 18, or even 24) months. Reference to the suitable storage container means a vessel that can retain the composition in its entirety without substantial loss of the volatile solvent.

Reference to a "film-former" includes a substance, such as a polymer, that forms a layer or film on a substrate after application of the composition thereto, is compatible with the delivery vehicle, and can keep the active ingredient in place on the location of application. The film-former provides, for example, a desirable consistency to the composition and allows delivery of the active ingredient over a timeframe after application. In a detailed embodiment, the film-former, also referred to as a thickener, comprises a hydrocolloid, a hydrocolloid derivative or combinations thereof. In one embodiment, the film-former comprises starch, pectin, agar, a cellulose, a cellulose derivative, a carrageenan, galactan, an alginate, agarose, xanthan gum, or combinations thereof. Another embodiment has the cellulose or the cellulose derivative comprising hydroxypropyl cellulose (HPC), hydroxyethyl cellulose (HEC), methyl cellulose (MC), carboxymethyl cellulose (CMC), or combinations thereof.

In a specific embodiment, the film-former has a cloud point (Cp) in the composition of from approximately 30° C. to approximately 100° C.; specifically from 40 to 70° C., more specifically from 45 to 55° C.

In one or more embodiments, the delivery vehicle further comprises a plasticizer comprising propylene glycol, glycerol, diethylene glycol monoethyl ether, dipropylene glycol, 2-methyl-2,4-pentanediol (MPD), propyl acetate, anisole, or combinations thereof.

In one or more embodiments, the biologically active agent is an antibacterial agent, an antimycotic agent, an antiviral agent, a cytostatic agent, a diuretic agent, an immuno modulator, a local anesthetic, an anti-inflammatory agent, a psoriatic agent, a derivative thereof, a prodrug thereof, a salt thereof, or combinations thereof.

In a detailed embodiment, the biologically active agent comprises terbinafine, naftifine, amorolfine, butenafine, derivatives thereof, prodrugs thereof, salts thereof, or combinations thereof. Terbinafine is present in one or more embodiments in an amount of from approximately 0.1 to approximately 10% by weight in the composition, more specifically from 0.5 to 5% and most specifically from 2 to 4%.

In a further aspect, provided is a composition effective for treating onychomycosis comprising terbinafine, acetone, citric acid, glycerol, and a film-former. In a detailed embodiment, the composition comprises terbinafine in an amount in the range of 2-10% by weight, acetone in an amount in the range of 10-50% by weight, citric acid in an amount in the range of 1-10% by weight, glycerol in an amount in the range of 1-10% by weight, and the film-former in an amount in the range of 2-8% by weight. An exemplary composition is a gel, which in an embodiment forms a lacquer after application. An exemplary film-former is hydroxyethyl cellulose. In a detailed embodiment, the composition remains stable in a suitable storage container for a period of about 12 months, or longer. In another detailed embodiment, the composition remains stable in a suitable storage container for a period of about 24 months, or longer. Also provided is a stable supersaturated film formed from a composition of terbinafine, acetone, citric acid, glycerol, and a film-former.

In another detailed embodiment, the biologically active agent comprises acyclovir, a derivative thereof, a prodrug thereof, a salt thereof, or combinations thereof. The acyclovir is present in one or more embodiments in an amount of from approximately 0.01 to approximately 10% by weight in the composition, more specifically from 0.05 to 5% and most specifically from 0.1 to 0.5%.

In one embodiment, the non-polymeric crystallization inhibitor is present in an amount of from approximately 5 to approximately 15% by weight in the composition. In another embodiment, the volatile component is present in an amount of from approximately 10 to approximately 95% by weight in the composition. In a further embodiment, the film-former is present in an amount of from approximately 0.5 to approximately 5% by weight in the composition. In yet another embodiment, the plasticizer is present in an amount of from approximately 5 to approximately 15% by weight in the composition.

Other embodiments may provide for a delivery vehicle further comprising a pharmaceutically acceptable excipient, a penetration enhancer, a keratolytic or avulsing agent, a chaotropic substance, a fragrance, an emollient, or combinations thereof.

In another aspect, a kit is provided. The kit comprises a single phase pharmaceutical composition comprising: a biologically active agent; a delivery vehicle comprising a non-polymeric crystallization inhibitor that is capable of delaying crystallization of the biologically active agent and a film-former; and a volatile solvent; wherein the biologically active agent is present in the composition in a subsaturated state, and wherein the biologically active agent is in a supersaturated state in the delivery vehicle; and an applicator for applying the composition to an area that is in need of the biologically active agent.

In another aspect, a pharmaceutically acceptable composition, such as a gel, lotion, cream, ointment, aerosol, or pump spray is provided.

A further aspect of the present invention includes the use of the compositions, wherein the biologically active agent is terbinafine, or a derivative, prodrug or salt thereof, for the manufacture of a medicament for treatment or prevention of onychomycosis. A method of treating onychomycosis is also provided, which comprises administering a supersaturated antifungal agent. In one embodiment, the method further comprises applying to a topical area in need of such treatment a single phase composition comprising terbinafine, naftifine, amorolfine, butenafine, derivatives thereof, prodrugs thereof, salts thereof, or combinations thereof in a therapeutically effective amount; a delivery vehicle comprising a film-former and a non-polymeric crystallization inhibitor; and a volatile solvent; wherein the terbinafine, or a derivative, a prodrug or a salt thereof is present in the composition in a subsaturated state; evaporating the volatile solvent; and providing the terbinafine, derivative, prodrug, or salt thereof in a supersaturated state in the delivery vehicle upon evaporation of the volatile solvent.

An additional aspect includes the use of the compositions, wherein the biologically active agent is acyclovir, or a derivative, prodrug or salt thereof, for the manufacture of a medicament for treatment or prevention of Varicella zoster infection, HSV-1 infection or HSV-2 infection. A method of treating or preventing Varicella zoster infection, HSV-1 infection or HSV-2 infection is also provided, which comprises administering a supersaturated antiviral agent. In one embodiment, the method further comprises applying to a topical area in need of such treatment a single phase composition comprising acyclovir, or a derivative, a prodrug or a salt thereof, in a therapeutically effective amount; a delivery vehicle comprising a film-former and a non-polymeric crystallization inhibitor; and a volatile solvent; wherein the acyclovir, or derivative, prodrug or salt thereof, is present in the composition in a subsaturated state; evaporating the volatile solvent; and providing the acyclovir, derivative, prodrug, or salt thereof and the delivery vehicle such that the acyclovir, derivative, prodrug, or salt thereof is in a supersaturated state in the delivery vehicle upon evaporation of the volatile solvent.

In a further aspect, a method of manufacturing a single phase topical composition is provided. The method comprises providing a biologically active agent; providing a delivery vehicle comprising a non-polymeric crystallization inhibitor that is capable of delaying crystallization of the biologically active agent in the delivery vehicle; providing a volatile solvent; and mixing the biologically active agent, the delivery vehicle, and the volatile solvent to form the composition wherein the biologically active agent is present in the composition in a subsaturated state and the biologically active agent is present in the delivery vehicle in a supersaturated state.

DETAILED DESCRIPTION

Topical compositions containing biologically active agents according to embodiments of the present invention provide unexpected stability and/or high delivery rate. Without intending to be limited by theory, aspects of the disclosed invention work according to the principle that evaporation of a volatile component from the composition results in enhanced thermodynamic activity of the biologically active agent in the delivery vehicle.

According to an embodiment of the present invention, the biologically active agent is present in the composition in a subsaturated state, thereby ensuring a physically stable product over its shelf-life by preventing precipitation of the active agent in the composition. When the volatile component evaporates, the thermodynamic activity of the biologically active agent in the delivery vehicle will increase, specifically to a level corresponding to a supersaturated state. Hence, the flux of the drug through a barrier such as skin, nails, and/or hooves, is increased in comparison with subsaturated and saturated systems.

The higher the degree of saturation of a substance in a mixture, the higher the desire for the substance to leave the mixture will be (i.e. the release of a substance from a mixture will be higher if the substance is supersaturated compared to being subsaturated). A supersaturated state is, however, by definition physically unstable and precipitation (i.e phase separation of the substance present in supersaturated state in the form of a separate liquid or a solid phase) will eventually occur. The higher the degree of supersaturation of a substance in a mixture the more prone to precipitation the substance will be.

In Vitro Release Testing (IVRT) can be used to evaluate flux of a composition over various membranes using a variety of media. Suitable membranes include natural and synthetic membranes. Natural membranes include, but are not limited to, bovine hooves, porcine ear skins, porcine hooves, equine hooves, and the like. Synthetic membranes include, but are not limited to, silastic, tuffryn, Teflon, nylon, fluoropore and other membranes. Examples of media, also referred to as receptor solutions, include, but are not limited to, phosphate-buffered saline and citrate buffer solution.

The use of a crystallization inhibitor in the compositions permits a higher degree of supersaturation of an active agent, which, in turn, renders a higher local concentration of the agent in the tissues of interest.

The topical compositions according to one or more embodiments of the invention are applied to areas in need of treatment, allowing easy or unimpeded evaporation into surrounding air of the volatile component of the composition. The term "topical" relates to "dermal, transdermal, ungual and transungual."

A film-former present in one or more embodiments of the present invention aids in retaining the topical composition, and thereby, the biologically active agent, in the area in need of treatment. Accordingly, it has been found that the solubility of the film-former in the composition impacts the magnitude of active agent release after evaporation of the volatile solvent. It has been found that optimum active agent release is achieved with a thickening polymer as poorly soluble in the composition as possible while still providing a homogeneous/single phase product. Methods for modifying the polymer solubility in a composition are elaborated on below.

The behavior of a polymer in a solution (which may herein be represented by the biologically active compositions of aspects of the invention) is strongly dependent on the properties of the solvent. In a good solvent, the polymer is free to extend and occupy a large volume. In a poor solvent, the polymer will contract to occupy a small volume. In an intermediate type of solvent the solubility of the polymer is moderate, i.e. neither good nor poor.

Depending on the type of polymer and its functional groups, phase separation from a solution can be induced either by a decrease or by an increase in temperature. Based on this concept, a critical temperature, $T_c$, can be defined, above which temperature the polymer is soluble in the solvent. $T_c$, for a given polymer is, however, also dependent on the degree of polymerization and there is therefore a large temperature interval over which the monomer ought to be infinitely soluble, while the corresponding polymer is only partly soluble.

Clouding is another unexpected thermotropic phenomenon that may limit the solubility of several polymers. Typically, solubility increases with increasing temperature. Clouding is a phase separation, however, that occurs on temperature increase beyond a critical temperature to the cloud point (herein denoted $C_p$). The mechanism behind this phase separation can be attributed to the fact that water becomes a poorer solvent for polar groups, in general, as the temperature increases.

Thus, the cloud point ($C_p$) is a suitable and practical parameter for determining whether a viscosity enhancing polymer in a composition represents a system wherein the polymer is moderately soluble in the composition while still providing a homogenous product.

Phase separation in terms of either the critical temperature ($T_c$) or the cloud point ($C_p$), depending on the type of polymer used, is determined in a specific composition only. That is, phase separation due to potential concentration dependence outside the ranges of the specific composition is neglected. There is phase separation if $T<T_c$ or if $T>C_p$. For any given polymer, either $T_c$, or $C_p$ is observed.

Phase separation may be defined by overnight storage of samples in sealed glass vials at defined temperatures (e.g. at 5° C. intervals) followed by visual inspection the day after. Phase separation is concluded if a previously clear composition turns cloudy or opaque overnight, a pre-stage for macroscopic phase separation. Reference to "phase separation" includes precipitation of any ingredient of the composition, such as the active ingredient, the crystallization inhibitor, the film-former, or combinations thereof.

Thus, according to certain embodiments of the present invention, it has been identified how the unexpected observation that a limited solubility of the polymer in a composition favors the release of a biologically active ingredient from the delivery vehicle after evaporation of the volatile part, as compared to a composition in which the polymer is freely soluble within a pharmaceutically relevant temperature interval.

This embodiment of the present invention thus describes how to limit the solubility in the composition of the viscosity increasing polymer, while providing a product that is macroscopically homogeneous over a temperature interval relevant from shelf-life perspective [see, e.g., *Note for Guidance on Declaration of Storage Conditions* EMEA/CPMP/QWP/609/96/revl], thereby facilitating the release of the biological active agent from the delivery vehicle post application.

Various means of modifying the solubility of the polymer in the surrounding media may comprise, but are not limited to, alteration of polymer chain length, switch to a related polymer, change of type of buffer and buffer concentration, addition of electrolytes, use of non-solvents, chaotropic (water structure breaking; Wood J. M., *Osmosensing by Bacteria: Signals and Membrane-Based Sensors*, Microbiol. Mol. Biol. Rev., March 1999, p. 230-262, Vol. 63, No. 1) substances, kosmotropic (water structure making; Wood J. M., supra) substances, change in pH, etc.

Crystallization inhibitors employed in the delivery vehicle of the topical compositions of the invention are selected so as to delay crystallization of the supersaturated biologically active agent in the delivery vehicle. Such delay may extend at least over a therapeutically relevant time frame, such as over 0-24 hours and more specifically 0-12 hours, after topical administration of the biologically active composition. The crystallization inhibitors are non-polymeric but may be either monomeric or oligomeric. As used herein, "polymeric" refers to molecules comprising more than 10 monomeric units whereas "oligomeric" refers to molecules comprising 2 to 10 monomeric units.

A standard procedure for in vitro testing for stability in the presence of crystallization inhibitors includes casting polymeric film (e.g., polyethylene) in the bottom of a Petri dish, applying a test gel or composition containing a crystallization inhibitor candidate evenly over the film in the bottom of the Petri dish (~160 mg/cm$^2$), placing the Petri dish containing the test gel in a 32° C. cabinet or oven overnight (~18±1 hr); and examining the test gel under a microscope to determine the presence of crystals visually. Magnifications of 10 to 100× are used. If there are no crystals, then the crystallization inhibitor candidate qualifies as a crystallization inhibitor.

Such a crystallization inhibitor may comprise an organic acid, e.g., a hydroxycarboxylic acid, specifically an α-hydroxy acid (e.g., citric acid, malic acid, or lactic acid), alone or in combination with a suitable plasticizer (herein defined as a substance that significantly lowers the glass transition temperature for a material to which it is added, thus making it softer and more pliable), e.g. a low molecular weight di- or trialcohol (e.g. dipropylene glycol or glycerol). Alternatively, such a crystallization inhibitor may be an oligomeric ester of the previously mentioned substances, and mixtures thereof, wherein the previously mentioned substances also may be present in monomeric form in amounts <20% (w/w). A further embodiment provides a polyol, for example, maltitol, as the crystallization inhibitor.

Another crystallization inhibitor may be selected from the group of mono- or oligosacharides, or mixtures thereof.

A suitable crystallization inhibitor may comprise citric acid, or esters and/or oligoesters thereof, as a glass-forming substance, in the range of 10-95 percent by weight and a plasticizer comprising propylene glycol or glycerol in the range of 5-90 percent by weight, where percentages by weight are based on the combined weight of glass-forming substance and plasticizer. In another embodiment, a suitable crystallization inhibitor may comprise esters and/or polyesters of citric acid and the plasticizers, obtained by chemical reaction(s) as described elsewhere (WO 99/58109, U.S. Pat. No. 6,537,576). It deserves to be mentioned, that regulation of the molecular weight, and distribution thereof, of the molecules which constitute the so formed crystallization inhibitor allows for controlling the solubility of the biologically active agent in the matrix. In one embodiment, the crystallization inhibitor is an oligomer of citric acid and propylene glycol where the oligomeric esters have a monomer count of 2 to 8 and a degree of esterification is approximately 30 to 100%. Monofunctional monomers can be introduced into the chemical reaction(s) as a means of controlling the end point of the reaction(s). As a non-limiting example, the crystallization inhibitor may contain a minor amount of starting substance(s), and still be within the scope of the present invention. A starting substance is, for example, a monomer, e.g., citric acid or propylene glycol. Generally this means that the ester or polyester forming reaction(s) is (are) performed in the absence of the biologically active agent.

Film-formers, also referred to as thickening or viscosity-increasing polymers, employed in the delivery vehicles provide, for example, a desirable consistency to the composition and allow delivery of the biologically active substance over a prolonged period of time. They are typically pharmaceutically acceptable hydrocolloids (e.g. polysaccharides).

An example of a suitable film-former is a natural hydrocolloid such as starch, cellulose, pectin, agar, carragenans, galactan, alginates, or agarose. Another example of a suitable viscosity-increasing polymer is a chemically modified hydrocolloid such as an anionic or a nonionic cellulose derivative. A suitable anionic cellulose derivative is a carboxy methyl cellulose (CMC). Suitable non-ionic cellulose derivatives include hydroxyalkyl cellulose derivatives such as those described in WO00/24966, directed to hydrophobically-modified water-soluble or water-swellable polymers. Specific examples of such derivatives are i) methyl cellulose, hydroxypropyl cellulose, hydroxypropylmethyl cellulose, hydroxyethyl cellulose, and ethyl hydroxyethyl cellulose; and ii) hydrophobically modified methyl cellulose and hydrophobically modified hydroxypropyl cellulose.

The volatile solvent is selected according to principles well known to a skilled artisan so as to achieve a pharmaceutically acceptable rate of evaporation and to provide an environment that keeps the crystallization inhibitor functionally stable over the composition's shelf-life. Similarly, according to principles well known to one skilled in the art, the solubility of the biologically active agent in the composition has to be sufficiently high to allow a high degree of saturation of the active substance in the delivery vehicle post-application.

Accordingly, suitable solvents comprise acetic acid, acetone, 1-butanol, 2-butanol, butyl acetate, tert-butylmethyl ether, ethanol, ethyl acetate, ethyl ether, ethyl formate, formic acid, heptane, isobutyl acetate, isopropyl acetate, methyl acetate, methylethyl ketone, methylisobutyl ketone, 2-methyl-1-propanol, pentane, 1-propanol, 2-propanol, propylacetate, water, n-butyl ether, isopropanol, or combinations thereof.

The solvent can be used individually or in mixtures. Other types of solvents can be included in minor portions in order to modify the solubility properties of the solvent mixture.

The biologically active agent may, according to embodiments of the present invention, be any pharmaceutically active agent intended for topical administration to a mammal, the mammal being human or animal. The choice of active agent is generally not limited. Biologically active agents are exemplified by agents intended for dermal, ungual, sub-lingual, gingival, buccal, transdermal, transungual, nasal, vaginal and rectal administration, whereby the resulting biological effect may be local and/or systemic. Pharmaceutically active agents suitable for delivery by the biologically active composition of the invention are exemplified by, but not limited to, antibacterial agents (e.g. metronidazole, clindamycine), antimycotic agents (e.g. clotrimazole, econazole, terbinafine, fluconazole, amorolfine, itraconazole, ketoconazole), antiviral agents (e.g. acyclovir, penciclovir, cidofovir, brivudin), cytostatic agents (e.g. methotrexate, 5-fluorouracil), diuretic agents (e.g. spironolactone), immuno modulators (e.g. cyclosporin, mycophenolic acid, mycophenolate mofetil, tacrolimus, pimecrolimus), local anesthetics (e.g. lidocaine, bupivacaine), antiinflammatory agents (e.g. piroxicam, diclofenac, tacrolimus, pimecrolimus), psoriatic agents (e.g. tazarotene, dithranol), or derivatives, prodrugs or salts thereof. Particularly suitable are immuno modulators and anti-inflammatory agents.

Hence, embodiments of the invention also relate to topical biologically active single phase compositions as described herein for use as medicaments.

An embodiment of the invention is when the biologically active agent is terbinafine, or a derivative, prodrug or salt thereof, specifically in a concentration of from 0.1 to 10%, more specifically from 0.5 to 5% and most specifically from 1 to 3%, by weight of the total composition. Thus, the invention also relates to the use of a topical biologically active single phase composition as defined herein, wherein the biologically active agent is terbinafine, or a derivative, prodrug or salt thereof, for the manufacture of a medicament for treatment or prevention of onychomycosis. In this embodiment of the invention, it is preferred to include avulsers and/or keratolytic agents, as further discussed below, in the composition. Alternatively, the invention also relates to a method of treating or preventing onychomycosis, which comprises administering to a patient in need of such treatment a topical biologically active single phase composition as defined herein, wherein the biologically active agent is terbinafine, or a derivative, prodrug or salt thereof, in a therapeutically effective amount.

Another embodiment of the invention is when the biologically active agent is acyclovir, or a derivative, prodrug or salt thereof, specifically in a concentration of from 0.01 to 10%, more specifically from 0.05 to 5% and most specifically from 0.1 to 0.5%, by weight of the total composition. Thus, embodiments of the invention also relate to the use of a topical biologically active single phase composition as defined herein, wherein the biologically active agent is acyclovir, or a derivative, prodrug or salt thereof, for the manufacture of a medicament for treatment or prevention of Varicella zoster infection, HSV-1 infection or HSV-2 infection. Alternatively, the invention also relates to a method of treating or preventing Varicella zoster infection, HSV-1 infection or HSV-2 infection, which comprises administering to a patient in need of such treatment a topical biologically active single phase composition as defined herein, wherein the biologically active agent is acyclovir, or a derivative, prodrug or salt thereof, in a therapeutically effective amount.

In an embodiment of the invention, the composition further comprises a penetration enhancer. The aim is to reversibly alter the properties of the biological barriers, such as skin or mucosa, in order to facilitate the drug delivery. The penetration enhancer may be chosen from simple alkyl esters, phospholipids, terpenes, non-ionic surfactants, azacycloheptanones (e.g. azone and its derivatives), oleyl surfactants, etc. Examples of suitable penetration enhancers are given in "Pharmaceutical skin penetration enhancement", Walters K. A. and Hadgraft J., eds., Marcel Dekker N.Y., 1993, and "Percutaneous penetration enhancers", 2 ed., Smith E. W. and Maibach H. I., eds., CRC Press, 2005.

Further enhancement of penetration through the nail, besides the effect of an enhanced thermodynamic activity of the biologically active substance, may be generated by inclusion of keratolytic agents, so-called avulsers, in the composition, as exemplified by urea, acetylcysteine and thioacids.

Inclusion of a chaotropic substance may further improve penetration through changes in the hydrophobic interactions (disrupting the regular hydrogen-bond structures in water and breaking hydrophobic hydrogen-bonded complexes). The chaotropic substance may be exemplified by urea, allantoin or guanidine.

Additional excipients may be added to the composition in order to render it pharmaceutically acceptable, such as alternative buffers to adjust pH, preservatives (e.g., sodium benzoate), etc.

Aspects of the present invention additionally relate to a pharmaceutically acceptable composition, such as a gel, lotion, cream or ointment, comprising a topical biologically active single phase composition as defined herein.

For some biologically active agents, it is preferred to prepare a composition shortly before administration thereof. Indeed, the compositions are useful for such preparations in addition to being suitable for compositions intended for long-term storage and application.

EXAMPLES

The following non-limiting examples will further illustrate the present invention. In the examples the term "room temperature" relates to a temperature in the range of 15-30° C., typically in the range of 18-28° C.

Example 1

A terbinafine 3% gel of the composition in Table 1a was prepared in a beaker at room temperature according to the following steps: i) citric acid and sodium hydroxide were dissolved in water, ii) glycerol, acetone and terbinafine were added, iii) hydroxyethyl cellulose was added under vigorous stirring, and iv) after obtaining a homogeneous gel, the composition was left to equilibrate for 24 hours, thereby permitting, for example, the hydroxyethyl cellulose to swell and any air bubbles to dissipate.

TABLE 1a

|  | % (w/w) |
|---|---|
| Terbinafine HCl | 3.0 |
| Acetone | 30.0 |
| Citric acid | 5.0 |
| Hydroxyethyl cellulose | 4.0 |
| Glycerol | 2.5 |
| Sodium hydroxide | 0.9 |
| Water | to 100 |

In vitro permeation of three terbinafine compositions was performed over bovine hoof membranes, using Franz diffusion cells and a receptor solution of degassed buffer solution. For each test membrane, test composition was applied with a brush. The in vitro permeation of terbinafine over bovine hooves from this terbinafine 3% gel was compared to that from Lamisil Dermgel 1% (Novartis, Lot F00049A) and Lamisil Cream 1% (Novartis, Lot WC114). Mean values of cumulative amount penetrated after 6 hours and standard deviations of triplicate samples are shown in Table 1b. The amount of penetrated terbinafine ($\mu g/cm^2$) was calculated by multiplying the concentration of terbinafine in the receptor solution with the volume of the cell and dividing by the membrane area. The flux was calculated by dividing the amount of penetrated terbinafine with the time of the experiment.

Because viscosity of the delivery vehicle was too high to permit solubility and saturation levels to be determined, penetration data of Table 1b was used to infer saturation levels. It is well-known that initial penetration of a drug through an inert membrane is dependent only on the saturation level of the drug and not its concentration. Thus, penetration data obtained from standard saturated solutions of the drug (e.g., Lamisil Dermgel 1% and Lamisil Cream 1% of Table 1b) was compared with data derived from exemplary compositions according to the present invention (e.g., Terbinafine 3% gel of Table 1b) to determine the relative saturation levels. Because the cumulative amount achieved with Terbinafine 3% gel was greater than that achieved with Lamisil Dermgel 1% and Lamisil Cream 1%, the Terbinafine 3% gel were more saturated, e.g., supersaturated, relative to the saturated Lamisil examples.

TABLE 1b

|  | Cumulative amount (n = 3) $\mu g/cm^2$ | Flux (n = 3) $\mu g/cm^2 h$ |
|---|---|---|
| Terbinafine 3% gel | 8.14 ± 1.20 | 1.36 ± 0.20 |
| Lamisil Dermgel 1% | 0.08 ± 0.06 | 0.01 ± 0.01 |
| Lamisil Cream 1% | 0.11 ± 0.06 | 0.02 ± 0.01 |

Example 2

Clinical Study

The results of the use of terbinafine 3% gel in treatment of onychomycosis of the toenail were obtained from an open label study. In this study, patients with onychomycosis were treated with terbinafine 3% gel or vehicle only for 42 days. The day 42 study results showed that 39.3% of the treatment subjects who were KOH positive at baseline were converted to being negative at day 42. The 42.8% treatment subjects who showed PAS positivist baseline were negative at completion. The 95.2% who were culture positive for dermatophytes at baseline were negative at completion. Mean concentration of terbinafine in the nail beds (n=4-5 per time point) was 2898 ng/mg on Day 14; 2640 ng/mg on Day 28; and 795 ng/mg on Day 42. After topical application of terbinafine nail lacquer 3%, terbinafine penetrates the nail plate in sufficient amounts to have efficacy for the treatment of onychomycosis.

Example 3

The acyclovir 0.1% gels of compositions A and B, respectively, in Table 3a were prepared in a beaker at room temperature according to the following steps: i) acyclovir, crystallization inhibitor (oligomeric citrate esters) and sodium benzoate were dissolved in water, ii) pH was adjusted with sodium hydroxide, iii) the mixture was heated to 45° C., iv) hydroxypropyl cellulose was added, v) the composition was allowed to cool to room temperature while stirring, vi) stirring was terminated after 2 hours.

TABLE 3a

|  | A % (w/w) | B % (w/w) |
|---|---|---|
| Acyclovir | 0.1 | 0.1 |
| Water | 92.7 | 82.6 |
| Crystallization inhibitor (oligomeric citrate esters) | 4.9 | 15.0 |
| Hydroxypropyl cellulose | 2.2 | 2.2 |
| Sodium benzoate | 0.1 | 0.1 |
| Sodium hydroxide | To pH 4 | To pH 4 |

The in vitro permeation of acyclovir over excised full thickness porcine ear skin from the acyclovir 0.1% gels A and B were compared to that from Zovirax cream 5% (Glaxo Wellcome, Lot 0021208). Mean values of 6-8 samples after 6.5 and 12.5 hours, respectively, are shown in Table 3b.

The penetration data of Table 3b was used to infer saturation. The data of the standard saturated solution of the drug (e.g., Zovirax cream 5% of Table 3b) was compared with data derived from exemplary compositions according to the present invention (e.g., Acyclovir 0.1% gels (A) and (B) of Table 3b) to determine the relative saturation levels. Because the cumulative amounts achieved with Acyclovir 0.1% gels (A) and (B) were greater than that achieved with Zovirax cream 5%, the Acyclovir 0.1% gels (A) and (B) were more saturated, e.g., supersaturated, relative to the saturated Zovirax example.

TABLE 3b

|  | Cumulative amount (n = 6-8) ng/cm² at 6.5 h | Cumulative amount (n = 6-8) ng/cm² at 12.5 h |
|---|---|---|
| Acyclovir 0.1% gel (A) | 815 | 899 |
| Acyclovir 0.1% gel (B) | 682 | 822 |
| Zovirax cream 5% | 5 | 35 |

Example 4

A series of compositions containing one of three thickening agents, a biologically active agent (acyclovir), a solvent mixture, and a crystallization inhibitor were manufactured and were allowed to equilibrate overnight at 32° C. The compositions are listed in Table 4a.

TABLE 4a

|  | A % (w/w) | B % (w/w) | C % (w/w) | D % (w/w) | E % (w/w) |
|---|---|---|---|---|---|
| Acyclovir | 0.20 | 0.25 | 0.20 | 0.25 | 0.25 |
| Ethanol | 20.1 | 20.0 | 20.0 | 20.0 | 20.0 |
| Crystallization inhibitor (oligomeric citrate esters) | 8.1 | 12.0 | 8.1 | 12.0 | 12.0 |
| Propylene glycol | 7.4 | 7.5 | 7.5 | 7.5 | 7.5 |
| Film-former HPC | 2.2 | 2.2 |  |  |  |
| Film-former HEC |  |  | 2.2 | 2.2 |  |
| Film-former MC |  |  |  |  | 2.2 |
| Citric acid | 1.9 | 2.9 | 1.9 | 2.9 | 2.9 |
| NaOH | 0.5 | 0.8 | 0.5 | 0.8 | 0.8 |
| Sodium benzoate | 0.1 | 0.1 | 0.1 | 0.1 | 0.1 |
| RO (reverse osmosis) water | to 100.0 | to 100.0 | to 100.0 | to 100.0 | to 100.0 |

HPC = Hydroxypropyl cellulose (Klucel ® MF Pharm)
HEC = Hydroxy ethyl cellulose (Natrosol ® 250M Pharm)
MC = Methyl cellulose (Methocel ™ E10M CR Premium)

In vitro permeation of the acyclovir compositions was performed over porcine inner ear skin membranes, using Bronaugh diffusion cells and a receptor solution of degassed phosphate-buffered saline (PBS). The compositions were tested for release rate in Bronaugh type cells. The cloud point was also determined, and these results are shown in Table 4b.

TABLE 4b

|  | A | B | C | D | E |
|---|---|---|---|---|---|
| Cloud point (° C.) | 35 < T < 40 | 40 < T < 45 | >100 | >100 | >100 |
| Cumulative amount ($\mu$g/cm²; 3 h) | 108 | 112 | 13 | 12 | 14 |
| Cumulative amount ($\mu$g/cm²; 6 h) | 135 | 131 | 19 | 23 | 33 |

Compositions A and B, both having cloud points below 45° C., provided superior flux of the active agent. As the $C_p$ decreases, therefore, the flux improves, but if $C_p$ gets too low, phase separation would be expected.

Example 5

A series of compositions containing hydroxy propyl cellulose (HPC, Klucel®MF Pharm) as a thickening agent, a biologically active agent (acyclovir), a solvent mixture of different ethanol concentrations, and a crystallization inhibitor was manufactured. The compositions are listed in Table 5a.

TABLE 5a

|  | A % (w/w) | B % (w/w) | C % (w/w) | D % (w/w) |
|---|---|---|---|---|
| Acyclovir | 0.20 | 0.25 | 0.20 | 0.25 |
| Ethanol | 20.1 | 20.0 | 30.0 | 30.1 |
| Crystallization inhibitor (oligomeric citrate sters) | 8.1 | 12.0 | 8.0 | 12.0 |
| Propylene glycol | 7.4 | 7.5 | 7.5 | 7.5 |
| Film-former HPC | 2.2 | 2.2 | 2.2 | 2.2 |
| Citric acid | 1.9 | 2.9 | 1.9 | 2.9 |
| NaOH | 0.5 | 0.8 | 0.5 | 0.8 |
| Sodium benzoate | 0.1 | 0.1 | 0.1 | 0.1 |
| RO water | to 100.0 | to 100.0 | to 100.0 | to 100.0 |

In vitro permeation of the acyclovir compositions was performed over porcine inner ear skin membranes, using Bronaugh diffusion cells and a receptor solution of degassed phosphate-buffered saline (PBS). The compositions were tested for release rate in Bronaugh type cells. Drug penetration through porcine ear skin with respect to initial ethanol content in the solvent mixture was determined. The cloud point was also determined, and the results are shown in Table 5b. Cloud point of the HPC film-former was a function of ethanol concentration.

TABLE 5b

|  | A | B | C | D |
|---|---|---|---|---|
| Cloud point (° C.) | 35 < T < 40 | 40 < T < 45 | T > 100 | T > 100 |
| Cumulative amount ($\mu$g/cm²; 3 h) | 108 | 112 | 66 | 73 |
| Cumulative amount ($\mu$g/cm²; 6 h) | 135 | 131 | 103 | 86 |

Compositions A and B, having cloud points within 35-45° C., provided superior flux of the active agent.

Example 6

Two compositions containing xanthan gum (X, Xantural 180) as thickening agent, a biologically active agent (acyclovir), a solvent mixture of different ethanol concentrations, and a crystallization inhibitor were manufactured. The compositions are listed in Table 6a.

TABLE 6a

|  | A % (w/w) | B % (w/w) |
|---|---|---|
| Acyclovir | 0.25 | 0.25 |
| Ethanol | 20.0 | 10.0 |
| Crystallization inhibitor (oligomeric citrate esters) | 12.0 | 12.0 |
| Propylene glycol | 7.5 | 7.5 |
| Film-former X | 1.0 | 1.0 |
| Citric acid | 2.9 | 2.9 |

TABLE 6a-continued

|  | A<br>% (w/w) | B<br>% (w/w) |
|---|---|---|
| NaOH | 0.8 | 0.8 |
| Sodium benzoate | 0.1 | 0.1 |
| RO water | to 100.0 | to 100.0 |

In vitro permeation of the acyclovir compositions was performed over porcine inner ear skin membranes, using Bronaugh diffusion cells and a receptor solution of degassed phosphate-buffered saline (PBS). The compositions were tested for release rate in Bronaugh type cells. Drug penetration through porcine ear skin with respect to initial ethanol content in the solvent mixture was determined, and the results are shown in Table 6b.

TABLE 6b

|  | A | B |
|---|---|---|
| Cumulative amount ($\mu g/cm^2$; 3 h) | 189 | 109 |
| Cumulative amount ($\mu g/cm^2$; 6 h) | 270 | 150 |

Composition A contained a higher amount of ethanol compared to composition B, and provided a superior flux of the active agent. Composition A, however, was also prone to phase separation. Therefore, the flux performance of a composition needs to be balanced with the composition's tendency to phase separate.

Example 7

Four acyclovir gels (Table 7a) were administered topically to six live domestic pigs (6, 2, and 0.5 hours prior to sacrificing the pigs). All compositions were applied randomly to the back of each pig at all three application times. After sacrifice, each skin site was individually washed, tape stripped, excised, frozen and sliced (10 slices à 50 μm thickness. All fractions were analyzed scintigraphically.

TABLE 7a

|  | A<br>% (w/w) | B<br>% (w/w) | C<br>% (w/w) | D<br>% (w/w) |
|---|---|---|---|---|
| Acyclovir | 0.20 | 0.25 | 0.25 | 0.25 |
| Ethanol | 25.0 | 22.5 | 25.0 | 35.7 |
| Citrate esters | 8.0 | 12.0 | 12.0 | — |
| Propylene glycol | 7.5 | 7.5 | 7.5 | 5.7 |
| Citric acid | 1.9 | 2.9 | 2.9 | 5.1 |
| NaOH | 0.47 | 0.75 | 0.75 | 1.3 |
| Sodium benzoate | 0.10 | 0.10 | 0.10 | 0.05 |
| Glycerol | — | — | — | 5.2 |
| Klucel ® (HPC) | 2.2 | 2.2 | 2.2 | 2.2 |
| Water | to 100 | to 100 | to 100 | to 100 |

A success criterion was a minimum acyclovir concentration in dermis of at least 0.3 μg/cm³ over 0.5 to 6 hours. The criterion was established based on in vitro $IC_{50}$ values from literature [O'Brien et al. "Acyclovir. An updated review of its antiviral activity, pharmacokinetic properties and therapeutic efficacy." *Drugs* 37 (1989) 233-309; Wagstaff et al. "Aciclovir; A reappraisal of its antiviral activity, pharmacokinetics properties and therapeutic efficacy." *Drugs* 47 (1994) 153-205]. For comparison, intravenous administration of 7.5-10 mg three times daily have produced serum concentrations of 5-10 μg/cm³, while 800 mg orally five times a day produced only 1-1.5 μg/cm³ acyclovir in serum [Herne et al. "Antiviral therapy of acute herpes zoster in older patients. *Drugs and Aging* Feb. 8:2 (1996) 97-112].

All compositions provided skin concentrations in dorsal porcine skin (0-500 μm) well above what has been reported in serum for high dose oral treatment (Table 7b). From mass balance considerations, it was also seen that the application dose may be decreased from 10 to 2-5 mg/cm².

TABLE 7b

|  | Cumulative amount μg/cm³ | | |
|---|---|---|---|
|  | 0.5 h | 2 h | 6 h |
| Acyclovir 0.20% gel (A) | 1.7 | 2.5 | 3.2 |
| Acyclovir 0.25% gel (B) | 2.4 | 2.5 | 4.6 |
| Acyclovir 0.25% gel (C) | 2.2 | 2.8 | 4.5 |
| Acyclovir 0.25% gel (D) | 3.1 | 3.9 | 5.3 |

Example 8

The following tables illustrate the versatility of embodiments of the present invention as well as additives that may be included to optimize the phase separation temperature (i.e. cloud point ($C_p$) or critical temperature ($T_c$) depending on the type of polymer) with respect to drug release.

TABLE 8a

|  | A % (w/w) | B % (w/w) | C % (w/w) | D % (w/w) | E % (w/w) | F % (w/w) | G % (w/w) | H % (w/w) |
|---|---|---|---|---|---|---|---|---|
| Ethanol | — | — | — | — | 40.0 | 40.0 | 40.0 | 40.0 |
| Acetone | — | 30.0 | — | 30.0 | — | 30.0 | — | — |
| Propylene glycol | — | — | 20.0 | 20.0 | — | — | 20.0 | 20.0 |
| Glycerol | — | 5.0 | 5.0 | — | 5.0 | — | — | 5.0 |
| Citric acid | 5.0 | 5.0 | 5.0 | 5.0 | 5.0 | 5.0 | 5.0 | 5.0 |
| Film-former HPC | 2.0 | 2.0 | 2.0 | 2.0 | 2.0 | 2.0 | 2.0 | 2.0 |
| Sodium hydroxide | 1.6 | 1.1 | 0.9 | 0.8 | 0.9 | 0.2 | 0.8 | 0.6 |
| RO water | to 100 | to 100 | to 100 | to 100 | to 100 | to 100 | To 100 | to 100 |

TABLE 8b

| | A | B | C | D | E | F | G | H |
|---|---|---|---|---|---|---|---|---|
| Cloud point (° C.) | 20 < T < 25 | 25 < T < 30 | 20 < T < 25 | T > 100 | T > 100 | T > 100 | T > 100 | T > 100 |

The cloud point may be adjusted in the temperature interval of 20-100° C. by altering the plasticizer-solvent compositions.

Example 9

Comparative Examples

Increasing an amount of the crystallization inhibitor in a composition can result in precipitation of both the plasticizer and the active ingredient. Samples A and B of Table 9a were observed 15 hours after preparation at 32° C. Sample A showed crystals of both citric acid and acyclovir. Sample B, with a similar amount of acyclovir, did not show any crystals.

TABLE 9a

| | A % (w/w) | B % (w/w) |
|---|---|---|
| Acyclovir | 0.24 | 0.25 |
| Citric Acid | 5.99 | 4.00 |
| NaOH | 1.28 | 0.89 |
| Propylene Glycol | 7.52 | 7.48 |
| Glycerol | 2.51 | 5.01 |
| Ethanol | 35.01 | 35.06 |
| Sodium Benzoate | 0.05 | 0.05 |
| Film-former HPC (Klucel ®) | 2.22 | 2.22 |
| RO water | to 100 | to 100 |

In the presence of the crystallization inhibitor, the amount of active ingredient affects the formation of crystals after evaporation of a volatile solvent. The samples Tables 9b, 9c, and 9d were observed at 1 hour, 4 hours, and 26 hours, respectively at 32° C.

Samples A and B of Table 9b showed no crystals in the film after evaporation. Sample C showed crystals after more than 7 hours. Sample D showed crystals after 1 hour.

TABLE 9b

| | A % (w/w) | B % (w/w) | C % (w/w) | D % (w/w) |
|---|---|---|---|---|
| Acyclovir | 0.13 | 0.19 | 0.25 | 0.32 |
| Citrate Ester | 8.00 | 8.00 | 8.00 | 8.00 |
| Citric Acid | 1.92 | 1.92 | 1.92 | 1.92 |
| NaOH | 0.47 | 0.47 | 0.47 | 0.47 |
| Film-former HPC (Klucel ®) | 2.20 | 2.20 | 2.20 | 2.20 |
| Propylene Glycol | 7.50 | 7.50 | 7.50 | 7.50 |
| Ethanol | 25.00 | 25.00 | 25.00 | 25.00 |
| Sodium Benzoate | 0.10 | 0.10 | 0.10 | 0.10 |
| RO water | to 100 | to 100 | to 100 | to 100 |

Sample A of Table 9c showed no crystals in the film after evaporation. Sample B showed crystals after more than 7 hours. Sample C showed crystals after 1 hour.

TABLE 9c

| | A % (w/w) | B % (w/w) | C % (w/w) |
|---|---|---|---|
| Acyclovir | 0.18 | 0.27 | 0.36 |
| Citrate Ester | 12.00 | 12.00 | 12.00 |
| Citric Acid | 2.88 | 2.88 | 2.88 |
| NaOH | 0.75 | 0.75 | 0.75 |
| Film-former HPC (Klucel ®) | 2.20 | 2.20 | 2.20 |
| Propylene Glycol | 7.50 | 7.50 | 7.50 |
| Ethanol | 22.50 | 22.50 | 22.50 |
| Sodium Benzoate | 0.10 | 0.10 | 0.10 |
| RO water | to 100 | to 100 | to 100 |

Samples A and B of Table 9d showed no crystals in the film after evaporation. Sample C showed crystals after 1 hour.

TABLE 9d

| | A % (w/w) | B % (w/w) | C % (w/w) |
|---|---|---|---|
| Acyclovir | 0.18 | 0.27 | 0.36 |
| Citrate Ester | 12.00 | 12.00 | 12.00 |
| Citric Acid | 2.88 | 2.88 | 2.88 |
| NaOH | 0.75 | 0.75 | 0.75 |
| Film-former HPC (Klucel ®) | 2.20 | 2.20 | 2.20 |
| Propylene Glycol | 7.50 | 7.50 | 7.50 |
| Ethanol | 25.00 | 25.00 | 25.00 |
| Sodium Benzoate | 0.10 | 0.10 | 0.10 |
| RO water | to 100 | to 100 | to 100 |

Example 10

Comparative Example

Acyclovir gel with different drug concentrations were prepared based on the idea that the more concentrated gels would precipitate and provide systems saturated in acyclovir. The saturation flux could then be related to the individual flux from gels with lower acyclovir concentrations. The 0.1% gel observed approximately 1.6 times higher flux than the 0.5 and 0.7% gels, indicating that 0.06% (w/w) acyclovir in this specific vehicle to give a saturated formulation post-evaporation.

TABLE 10a

| | A % (w/w) | B % (w/w) | C % (w/w) |
|---|---|---|---|
| Acyclovir | 0.1 | 0.5 | 0.7 |
| Citrate Ester | 8.0 | 8.0 | 8.0 |
| Citric Acid | 1.9 | 1.9 | 1.9 |
| NaOH | 0.5 | 0.5 | 0.5 |

TABLE 10a-continued

|  | A % (w/w) | B % (w/w) | C % (w/w) |
|---|---|---|---|
| Film-former HPC (Klucel ®) | 2.2 | 2.2 | 2.2 |
| Ethanol | 20.0 | 20.0 | 20.0 |
| Sodium Benzoate | 0.1 | 0.1 | 0.1 |
| RO water | to 100 | to 100 | to 100 |

Example 11

The following tables illustrate the versatility embodiments of the present invention. The hydrocolloids referred to in embodiments of the present invention are represented by specific polymers from each group: a natural hydrocolloid (xanthan gum); non-ionic cellulose derivatives (hydroxypropyl cellulose, HPC; hydroxyethyl cellulose, HEC; ethyl cellulose, EC); and an anionic cellulose derivative (carboxy methyl cellulose, CMC). Each one of these specific polymers may also occur in various modifications, having slightly different properties. The solubility properties of the biologically active agent determine which type of composition to use, as is understood by a person skilled in the art.

TABLE 11a

|  | A | B | C | D |
|---|---|---|---|---|
| Crystallization inhibitor 5-12% (w/w) | Lactic acid | Lactic acid | Diethyl citrate* | Citric acid |
| Plasticizer I 5-7.5% (w/w) | Propylene glycol | Glycerol | — | Glycerol |
| Plasticizer II 5-7.5% (w/w) | — | Propylene glycol | — | Propylene glycol |
| Solvent 10-35%(w/w) | Acetone | Ethanol | Acetone | Ethanol |
| Solvent to 100% (w/w) | Water | Water | Citrate Buffer 0.1 M | Water |
| Film-former 1-5% (w/w) | HEC | HPC | HEC | HPC |
| NaOH or HCl | To pH4 | To pH4 | To pH4 | To pH4 |

*Diethyl citrate (Citrofol ® Dec; a citric acid/diethyl citrate/triethylcitrate/ethanol 5/25/45/25 mixture)

TABLE 11b

|  | E | F | G | H | I |
|---|---|---|---|---|---|
| Crystallization inhibitor 5-12% (w/w) | Malic acid | Malic acid | Malic acid | Malic acid | Malic acid |
| Plasticizer I 5-7.5% (w/w) | Glycerol | Glycerol | Propyl acetate | Anisole | Transcutol |
| Plasticizer II 5-7.5% (w/w) | Propylene glycol | — | — | — | — |
| Solvent 10-35% (w/w) | Ethanol | Methyl acetate | 2-propanol | Methyl ethyl-ketone | Ethyl formate |
| Solvent to 100% (w/w) | Water | Water | Water | Acetone | Water |
| Film-former 1-5% (w/w) | HPC | CMC | HEC | EC | Xanthan |
| NaOH or HCl | To pH 4 | To pH 4 | To pH 4 | To pH 4 | To pH 4 |

TABLE 11c

|  | J | K | L | M | N |
|---|---|---|---|---|---|
| Crystallization inhibitor 5-12% (w/w) | Maltitol | Maltitol | Maltitol | Maltitol | Maltitol |
| Plasticizer I 5-7.5% (w/w) | Glycerol | Transcutol ®* | Glycerol | Dipropylene glycol | MPD** |
| Plasticizer II 5-7.5% (w/w) | Propylene glycol | — | — | — | — |
| Solvent 10-35% (w/w) | Ethanol | Acetone | Ethanol | 2-propanol | Methyl acetate |
| Solvent to 100% (w/w) | Buffer 0.1 M | Buffer 0.1 M | Buffer 0.1 M | Buffer 0.1 M | Buffer 0.1 M |
| Film-former 1-5% (w/w) | HPC | HEC | Xanthan | HPC | HPC |
| NaOH or HCl | To pH 4 | To pH 4 | To pH 4 | To pH 4 | To pH 4 |

*Transcutol ® = diethylene glycol monoethyl ether
**MPD = 2-methyl-2,4-pentanediol Example 12

Terbinafine 3% gels prepared as in Example 1 and having the composition in Table 1a were compared for stability purposes. In vitro permeation of these terbinafine compositions was performed over bovine hoof membranes as described in Example 1, however, for each test membrane, an amount of 200 mg/cm² of a test composition was applied. Table 12 shows the flux data after 6 hours, for two samples at 24 months after preparation and one sample at time <1 week after preparation. There was no significant difference in the penetration capacity and flux for terbinafine 3% gels that were stored for 24 months compared to a freshly made composition of <1 week.

TABLE 12

|  | Time after preparation | Cumulative amount (n = 3) µg/cm² | Flux (n = 3) µg/cm²h |
|---|---|---|---|
| Terbinafine 3% gel | <1 week | 29.19 ± 3.58 | 4.87 ± 0.60 |
| Terbinafine 3% gel | 24 months | 32.69 ± 5.16 | 5.45 ± 0.86 |
| Terbinafine 3% gel | 24 months | 31.91 ± 4.26 | 5.32 ± 0.71 |

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although embodiments of the invention herein have been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A single phase pharmaceutical composition for topical administration comprising:
   a biologically active agent selected from the group consisting of terbinafine, naftifine, amorolfine, butenafine, derivatives thereof, salts thereof, or combinations thereof;
   a delivery vehicle comprising a non-polymeric crystallization inhibitor that is capable of delaying crystallization of the biologically active agent, and a film-former; and
   a volatile solvent in an amount selected to create a subsaturated solution of said biologically active agent;
   water;
   wherein the biologically active agent attains a supersaturated state upon evaporation of the volatile solvent upon said administration.

2. The composition of claim 1, wherein the volatile solvent has a vapor pressure of 5 kappa or greater at 20° C.

3. The composition of claim 1, wherein the non-polymeric crystallization inhibitor comprises a hydroxycarboxylic acid.

4. The composition of claim 3, wherein the hydroxycarboxylic acid comprises citric acid, lactic acid, malic acid, or combinations thereof.

5. The composition of claim 1, wherein the non-polymeric crystallization inhibitor delays crystallization of the biologically active agent in the delivery vehicle up to approximately 24 hours after administration of the composition.

6. The composition of claim 1, wherein the volatile solvent comprises acetic acid, acetone, 1-butanol, 2-butanol, butyl acetate, tert-butylmethyl ether, ethanol, ethyl acetate, ethyl ether, ethyl formate, formic acid, heptanes, isobutyl acetate, isopropyl acetate, methyl acetate, methylethyl ketone, methylisobutyl ketone, 2-methyl-1-propanol, pentane, 1-propanol, 2-propanol, propylacetate, water, n-butyl ether, isopropanol or combinations thereof.

7. The composition of claim 1, wherein the film-former comprises a hydrocolloid, a hydrocolloid derivative, or combinations thereof.

8. The composition of claim 7, wherein the film-former comprises starch, pectin, agar, a cellulose, a cellulose derivative, a carrageenan, galactan, an alginate, agarose, xanthan gum, or combinations thereof.

9. The composition of claim 8, wherein the cellulose or the cellulose derivative comprises hydroxypropyl cellulose (HPC), hydroxyethyl cellulose (HEC), methyl cellulose (MC), carboxy methyl cellulose (CMC), or combinations thereof.

10. The composition of claim 1, wherein the film-former has a cloud point ($C_p$) in the composition of from approximately 30° C. to approximately 100° C.

11. The composition of claim 10, wherein the cloud point ($C_p$) is from approximately 40° C. to approximately 70° C.

12. The composition of claim 11, wherein the cloud point ($C_p$) is from approximately 45° C. to approximately 55° C.

13. The composition of claim 1, further comprising a plasticizer.

14. The composition of claim 13, wherein the plasticizer comprises propylene glycol, glycerol, diethylene glycol monoethyl ether, dipropylene glycol, 2-methyl-2,4-pentanediol (MPD), propyl acetate, anisole, or combinations thereof.

15. The composition of claim 1, wherein the biologically active agent is an antibacterial agent, an antimycotic agent, an antiviral agent, a cytostatic agent, a diuretic agent, an immune modulator, a local anesthetic, an anti-inflammatory agent, a psoriatic agent, a derivate thereof, a salt thereof, or combinations thereof.

16. The composition of claim 1, wherein the biologically active agent comprises terbinafine, the derivative thereof, the salt thereof, or combinations thereof and is present in an amount of from approximately 0.1 to approximately 10% by weight of the composition.

17. The composition of claim 13, wherein the biologically active agent comprises terbinafine, the non-polymeric crystallization inhibitor comprises citric acid, the volatile solvent comprises acetone, the film-former comprises hydroxyethyl cellulose, and the plasticizer comprises glycerol.

18. The composition of claim 1, wherein the non-polymeric crystallization inhibitor is present in an amount of from approximately 5 to approximately 15% by weight of the composition.

19. The composition of claim 1, wherein the volatile solvent is present in an amount of from approximately 10 to approximately 95% by weight in the composition.

20. The composition of claim 1, wherein the film-former is present in an amount of from approximately 0.5 to approximately 5% by weight in the composition.

21. The composition of claim 13, wherein the plasticizer is present in an amount of from approximately 5 to approximately 15% by weight in the composition.

22. The single-phase composition of claim 1 effective for treating onychomycosis wherein the biologically active agent is terbinafine, the volatile solvent is acetone, the crystallization inhibitor is citric acid, and wherein the composition further comprises water, and glycerol.

23. The composition of claim 22, comprising terbinafine in an amount in the range of 2-10% by weight, acetone in an amount in the range of 10-50% by weight, citric acid in an amount in the range of 1-10% by weight, glycerol in an amount in the range of 1-10% by weight, and the film-former in an amount in the range of 2-8% by weight.

24. The composition of claim 22, wherein the composition is a gel.

25. A kit comprising:
    a single phase pharmaceutical composition of claim 1; and
    an applicator for applying the composition to an area that is in need of the biologically active agent.

26. A pharmaceutically acceptable formulation, which is a gel, lotion, cream, ointment, aerosol, or pump spray comprising the composition of claim 1.

27. A method of treating or preventing onychomycosis, comprising applying the composition of claim 1, wherein the biologically active agent is terbinafine, naftifine, amorolfine, butenafine, derivatives thereof, salts thereof, or combinations thereof.

28. A method of treating onychomycosis, which comprises administering a supersaturated antifungal agent of claim 1.

29. The method of claim 28, further comprising:
applying to a topical area in need of such treatment a single phase composition comprising terbinafine, or a derivative, or a salt thereof, in a therapeutically effective amount; a delivery vehicle comprising a non-polymeric crystallization inhibitor and a film-former; and a volatile solvent; wherein the terbinafine, or a derivative, or a salt thereof is present in the composition in a subsaturated state;
evaporating the volatile solvent; and
wherein the administering step comprises providing the terbinafine, derivative, or salt thereof and the delivery vehicle such that the terbinafine, the derivative, or the salt thereof is in a supersaturated state in the delivery vehicle upon evaporation of the volatile solvent.

30. The method of claim 29, wherein the delivery vehicle further comprises a plasticizer.

31. The method of claim 29, wherein the biologically active agent comprises terbinafine, the non-polymeric crystallization inhibitor comprises citric acid, the volatile solvent comprises acetone, the film-former comprises hydroxyethyl cellulose, and the plasticizer comprises glycerol.

32. The method of claim 31, wherein the composition comprises terbinafine in an amount in the range of 2-10% by weight, acetone in an amount in the range of 10-50% by weight, citric acid in an amount in the range of 1-10% by weight, glycerol in an amount in the range of 1-10% by weight, and the film-former in an amount in the range of 2-8% by weight.

33. A method of manufacturing a single phase topical composition of claim 1, comprising:
providing a biologically active agent;
providing a delivery vehicle comprising a non-polymeric crystallization inhibitor that is capable of delaying crystallization of the biologically active agent in the delivery vehicle and a film-former;
providing a volatile solvent; and
mixing the biologically active agent, the delivery vehicle, and the volatile solvent to form the composition wherein the biologically active agent is present in the composition in a subsaturated state and the biologically active agent is present in the delivery vehicle in a supersaturated state.

34. The method of claim 33, wherein the biologically active agent comprises terbinafine, naftifine, amorolfine, butenafine, derivatives thereof, salts thereof, or combinations thereof.

35. The composition of claim 1, wherein the composition remains stable in a suitable storage container for a period of about 12 months, or longer.

36. The composition of claim 35, wherein the composition remains stable in a suitable storage container for a period of about 24 months, or longer.

37. A single phase pharmaceutical composition for topical administration comprising:
an antimycotic agent; and
a vehicle comprising a hydroxycarboxylic acid, glycerol, a cellulose derivative, water, and acetone;
wherein the hydroxycarboxylic acid is capable of delaying the crystallization of the antimycotic agent; and
wherein the antimycotic agent is present in the composition in a subsaturated state, and attains a supersaturated state upon evaporation of the acetone upon said administration.

38. The single phase pharmaceutical composition of claim 37, wherein the antimycotic agent is terbinafine.

39. The single phase pharmaceutical composition of claim 38, wherein the cellulose derivative is hydroxyethyl cellulose.

40. The single phase pharmaceutical composition of claim 39, comprising terbinafine in the range of 2-10% by weight, acetone in the range of 10-50% by weight, citric acid in the range of 1-10% by weight, glycerol in the range of 1-10% by weight, and hydroxyethyl cellulose in the range of 2-8% by weight.

41. The single phase pharmaceutical composition of claim 40, comprising: about 3% by weight terbinafine; about 30% by weight acetone; about 5% by weight citric acid; about 4% by weight hydroxyethyl cellulose; about 2.5% by weight glycerol; and further comprising about 0.9% by weight sodium hydroxide.

42. The single phase pharmaceutical composition of claim 37, which is in the form of a gel.

* * * * *